(12) United States Patent
Rootes et al.

(10) Patent No.: US 12,727,903 B2
(45) Date of Patent: Sep. 8, 2026

(54) IMPLANTABLE CHANNEL GUIDES AND METHODS AND KITS THEREOF

(71) Applicant: Covidien LP, Mansfield, MA (US)

(72) Inventors: Matthew A. Rootes, Crystal, MN (US); Nathan J. Knutson, Long Lake, MN (US)

(73) Assignee: Covidien LP, Mansfield, MA (US)

( * ) Notice: Subject to any disclaimer, the term of this patent is extended or adjusted under 35 U.S.C. 154(b) by 939 days.

(21) Appl. No.: 17/876,436

(22) Filed: Jul. 28, 2022

(65) Prior Publication Data

US 2023/0079131 A1 Mar. 16, 2023

Related U.S. Application Data

(60) Provisional application No. 63/243,242, filed on Sep. 13, 2021.

(51) Int. Cl.
*A61B 17/32* (2006.01)
*A61B 17/04* (2006.01)
*A61B 17/34* (2006.01)

(52) U.S. Cl.
CPC ...... *A61B 17/320016* (2013.01); *A61B 17/04* (2013.01); *A61B 2017/3484* (2013.01)

(58) Field of Classification Search
CPC ............ A61B 17/320016; A61B 17/04; A61B 2017/3484; A61B 1/2676; A61B 17/06166; A61B 90/96; A61B 2017/00809; A61B 2017/0441; A61B 2017/0464; A61B 2034/2051; A61F 2002/043; A61F 2/02
See application file for complete search history.

(56) References Cited

U.S. PATENT DOCUMENTS 2,820,566 A 1/1958 Hecke
6,004,330 A * 12/1999 Middleman ...... A61B 17/32056 606/127
6,514,290 B1 2/2003 Loomas
6,692,494 B1 2/2004 Cooper et al.
6,712,812 B2 3/2004 Roschak et al.
7,175,644 B2 2/2007 Cooper et al.
7,517,320 B2 4/2009 Wibowo et al.
7,985,187 B2 7/2011 Wibowo et al.
8,298,160 B2 10/2012 Oslund et al.
8,388,680 B2 3/2013 Starksen et al.
(Continued)

FOREIGN PATENT DOCUMENTS

DE 2425385 A1 12/1975
DE 202012101491 U1 8/2012
(Continued)

OTHER PUBLICATIONS

Extended European Search Report issued in European Patent Application No. 22195137.9 dated Feb. 10, 2023.

*Primary Examiner* — Charles A Marmor, II
*Assistant Examiner* — Marc D. Honrath
(74) *Attorney, Agent, or Firm* — Weber Rosselli & Cannon LLP

(57) ABSTRACT

The present disclosure describes an implantable channel guide configured to identify and/or a channel created in a patient via an endoscopic navigation procedure. The channel guide includes an elongate body having at least one snare on one end portion thereof and at least one anchor member on a second opposite end portion thereof.

19 Claims, 9 Drawing Sheets

(56) References Cited

U.S. PATENT DOCUMENTS 8,668,652 B2 3/2014 Wibowo et al.
8,721,734 B2 5/2014 Mathis et al.
9,474,533 B2 10/2016 Mathis et al.
10,188,398 B2 1/2019 Mathis et al.
10,376,261 B2 8/2019 Kosa et al.
10,537,334 B2 1/2020 Mathis et al.
2002/0042564 A1 4/2002 Cooper et al.
2003/0070676 A1 4/2003 Cooper et al.
2004/0073155 A1 4/2004 Laufer et al.
2005/0060041 A1 3/2005 Phan et al.
2005/0060042 A1 3/2005 Phan et al.
2005/0060044 A1 3/2005 Roschak et al.
2005/0137518 A1 6/2005 Biggs et al.
2005/0137611 A1 6/2005 Escudero et al.
2005/0137712 A1 6/2005 Biggs et al.
2005/0137715 A1 6/2005 Phan et al.
2005/0177144 A1 8/2005 Phan et al.
2005/0192526 A1 9/2005 Biggs et al.
2007/0096048 A1* 5/2007 Clerc ............... A61B 17/12104 251/142
2011/0071613 A1* 3/2011 Wood ........................ A61F 2/95 623/1.11
2013/0226026 A1* 8/2013 Dillard ................... A61B 10/02 604/174
2015/0190173 A1* 7/2015 Hiernaux ........... A61B 17/3478 606/185
2017/0281378 A1* 10/2017 Shintaku ................. A61F 2/915

FOREIGN PATENT DOCUMENTS

EP 0828574 A1 3/1998
TW 202123901 A * 7/2021 ............. A61L 27/56
WO WO-2020197854 A1 * 10/2020 ........... A61F 2/2466

* cited by examiner 230
215
230
212B
C"
C"
213
B"
B"
216
214
212a
218
222
222
220
220

213
215

214
215
216

IMPLANTABLE CHANNEL GUIDES AND METHODS AND KITS THEREOF

CROSS-REFERENCE TO RELATED APPLICATIONS

This application claims the benefit of the filing date of provisional U.S. Patent Application No. 63/243,242, filed Sep. 13, 2021, the entire contents of each of which are incorporated herein by reference.

BACKGROUND

Technical Field

The present disclosure is generally related to implantable channel guides, and more particularly, implantable channel guides configured to be used with electromagnetic navigation bronchoscopy.

Description of Related Art

Electromagnetic navigation bronchoscopy (ENB) is a diagnostic procedure in which an endoscope (e.g., bronchoscope), a catheter, an extended working channel (EWC), and/or an endoscopic surgical tools are navigated through the natural bronchial airways of the lung to a target tissue, e.g., a nodule or lesion, often positioned in the peripheral tissue beyond the airway. In such procedures, navigating from the airway to the target tissue, while avoiding sensitive tissues such as blood vessels, neighboring airways, and the like, can be difficult, time consuming, and/or require multiple steps.

As shown in FIG. 1A, during an ENB a endoscope 50, such as a bronchoscope, may be positioned within an airway 1 of patient's lung. A catheter and/or EWC 55 may extend from the endoscope 50 deeper into the airway 1. During the ENB, the catheter and/or EWC 55 may be navigated through the airway 1 to a target tissue 4 to allow for examination (visual, scanning, biopsy, etc.) of the target tissue 4. The catheter and/or EWC 55 may pass through the airway wall 2 and peripheral tissue 3 beyond the airway wall 2. Prior to the navigation process, a plurality of preplanning steps may occur to determine at least one pathway for the catheter and/or EWC 55 to follow to avoid piercing potentially sensitive tissues between the airway 1 and the target tissue 4. As the catheter and/or EWC 55 is advanced along the predetermined pathway, a channel 5 may be created through a portion of the airway wall 2, peripheral tissue 3, and/or target tissue 4. The channel 5 created is maintained while the catheter and/or EWC 55 remain in place and may initially remain following the removal of the catheter and/or EWC 55 (FIG. 1B). However, the channel 5 may be difficult to find and/or navigate in a subsequent surgical procedure because the channel 5 may naturally begin to close over time. In addition, removal of the catheter and/or the EWC 55 is necessary to prevent the catheter and/or EWC 55 from blocking the patient's airway 1 and making it difficult, if not impossible, for a patient to breathe through the airway 1 post-surgery.

Following a diagnosis of the target tissue 4 resulting from the initial ENB procedure, a subsequent surgical procedure may be recommended to treat the target tissue 4 (resection surgery, tissue ablation, supplemental biopsy, applying dyes or bioactive agents directly to target tissue, radioactive treatment, etc.). For example, in some instances, an ENB may be performed to biopsy a potentially cancerous lesion or nodule positioned off-airway of a patient's lung and the resulting diagnosis may recommend ablation of at least a portion of the lesion or nodule. However, the recommended subsequent ablation procedure may not occur for at least several days, weeks, or even months. Such procedures may also have to be repeated intermittently throughout a treatment cycle spanning over a period of days, weeks, or months.

Currently, navigation (or renavigation) of the catheter, EWC, and/or endoscopic surgical tool has to be performed prior to the subsequent surgical procedure being properly performed. It can be very difficult and time-consuming to find and/or renavigate through the exact same channel to arrive at the target tissue at the same position of the prior procedure.

Thus, there is a need for implantable channel guides configured to define the initial channel in the airway 1, airway wall 2, peripheral tissue 3, and/or target tissue 4 created during the ENB and remain implanted to maintain the channel at least generally, if not exactly. The benefits of such a channel guide include increased time efficiency of any subsequent procedure, as well as the increased likelihood of positioning the surgical tools at the same general, if not exact, position relative to the target tissue without any need for addition scanning, such as CT scanning, ultrasound, x-ray, electromagnetic, etc.

SUMMARY

The present disclosure describes an implantable channel guide configured to be used with an endoscope, a catheter, an EWC, and/or an endoscopic surgical tool. The guide is designed to identify and/or maintain a channel created in a patient's tissue during an endoscopic navigation procedure to ensure the channel can be reused during subsequent surgical procedures directed at the examination and/or treatment of the target tissue. The endoscope as described herein may be a bronchoscope.

An implantable channel guide as described herein may be configured for deployment at least partially in an airway of a patient. The guide may include an elongate body extending between a proximal end portion and a distal end portion, a snare extending from the proximal end portion of the elongate body, and an anchor member extending from the distal end portion of the elongate body. The elongate body may be configured to lead an endoscopic surgical tool through the airway to a target tissue.

In some embodiments, the implantable channel guide is configured for deployment at least partially in an airway of a patient and includes at least an elongate body, one or more snares, and one or more anchor members. The elongate body includes at least one lumen extending between a proximal end portion and distal end portion of the elongate body. The lumen is configured to pass endoscopic surgical tools therethrough to a target tissue. The at least one snare extends proximally from the proximal end portion of the elongate body, and the at least one anchor member extends distally from the distal end portion of the elongate body. The snare is configured to manipulate (e.g., rotate, withdraw, etc.) the guide. The anchor member is configured to secure the distal end portion of the body to at least one of the airway wall, peripheral tissue beyond the airway wall, and/or the target tissue.

In some embodiments, the at least one snare may include at least one loop or eyelet defining an opening therethrough. In some embodiments, the at least one snare may include two or more loop or eyelet snares positioned on opposite sides of the proximal end portion of the body.

In some embodiments, the elongate body is a porous tubular elongate body. The porous tubular elongate body may be formed from a plurality of yarns wrapping circumferentially around the lumen in a crisscrossing configuration and spaced about length of the body to define a plurality of surface pores therebetween. The yarns being interwoven using any suitable method to define the porous tubular elongate body.

The plurality of surface pores represent a majority of an outer surface area defined by the porous tubular elongate body and the plurality of yarns represent a minority of the outer surface area defined by the porous tubular elongate body. In some embodiments, the plurality of surface pores represent at least 85% of an outer surface area defined by the porous tubular elongate body and the plurality of yarns represent at most 15% of the outer surface area defined by the porous tubular elongate body.

In some embodiments, the porous tubular elongate body may be formed from a plurality of rods connected to a plurality of transverse ribs, the rods extending longitudinally and spaced circumferentially, the ribs extending circumferentially and spaced longitudinally.

In some embodiments, a proximal end portion of the guide (and/or elongate body) may include a porous tubular elongate body portion and a distal end portion of the guide (and/or elongate body) may include a non-porous tubular elongate body portion.

The implantable channel guides described herein may further include one or more necked portions. In some embodiments, the necked portions may include at least one of an extendable necked portion configured to lengthen when a longitudinal stress is applied thereto. In some embodiments, the necked portion may include a tearable necked portion configured to fracture when a longitudinal stress is applied thereto.

In some embodiments, the channel guide is configured to self-feed itself into the patient's tissue. In some embodiments, the channel guide is configured to expand into the patient's tissue upon exiting an endoscope, catheter or EWC.

In some embodiments, the implantable channel guides described herein may be configured for deployment at least partially in an airway of a patient and include an elongate body extending between a proximal end portion and an opposite distal end portion. The elongate body may be free of a lumen and configured to pass endoscopic surgical tools thereover to a target tissue. The lumen-free elongate body further includes at least one snare extending from the proximal end portion of the elongate body, and at least one anchor member extending from the distal end portion of the elongate body. The anchor member is configured to secure the distal end portion of the body to the target tissue. The anchor member may be a corkscrew anchor member.

Surgical kits are also provided. The surgical kits may include one or more implantable channel guides as described herein and at least one of an endoscope, a catheter, an EWC, a surgical navigation system, or an endoscopic surgical tool.

Surgical methods are also provided. The surgical methods may include: navigating at least one of an endoscope, catheter, or EWC through an airway of a patient to a target tissue beyond the airway; deploying an implantable channel guide via the at least one endoscope, catheter or EWC through a length of the airway to the target tissue; and removing the at least one endoscope, catheter or EWC from the airway while leaving the deployed channel guide extending a length through the patient's airway to the target tissue.

BRIEF DESCRIPTION OF THE DRAWINGS

Various aspects and features of the present disclosure are described herein below with reference to the drawings, wherein.

DETAILED DESCRIPTION

Figure 1A:
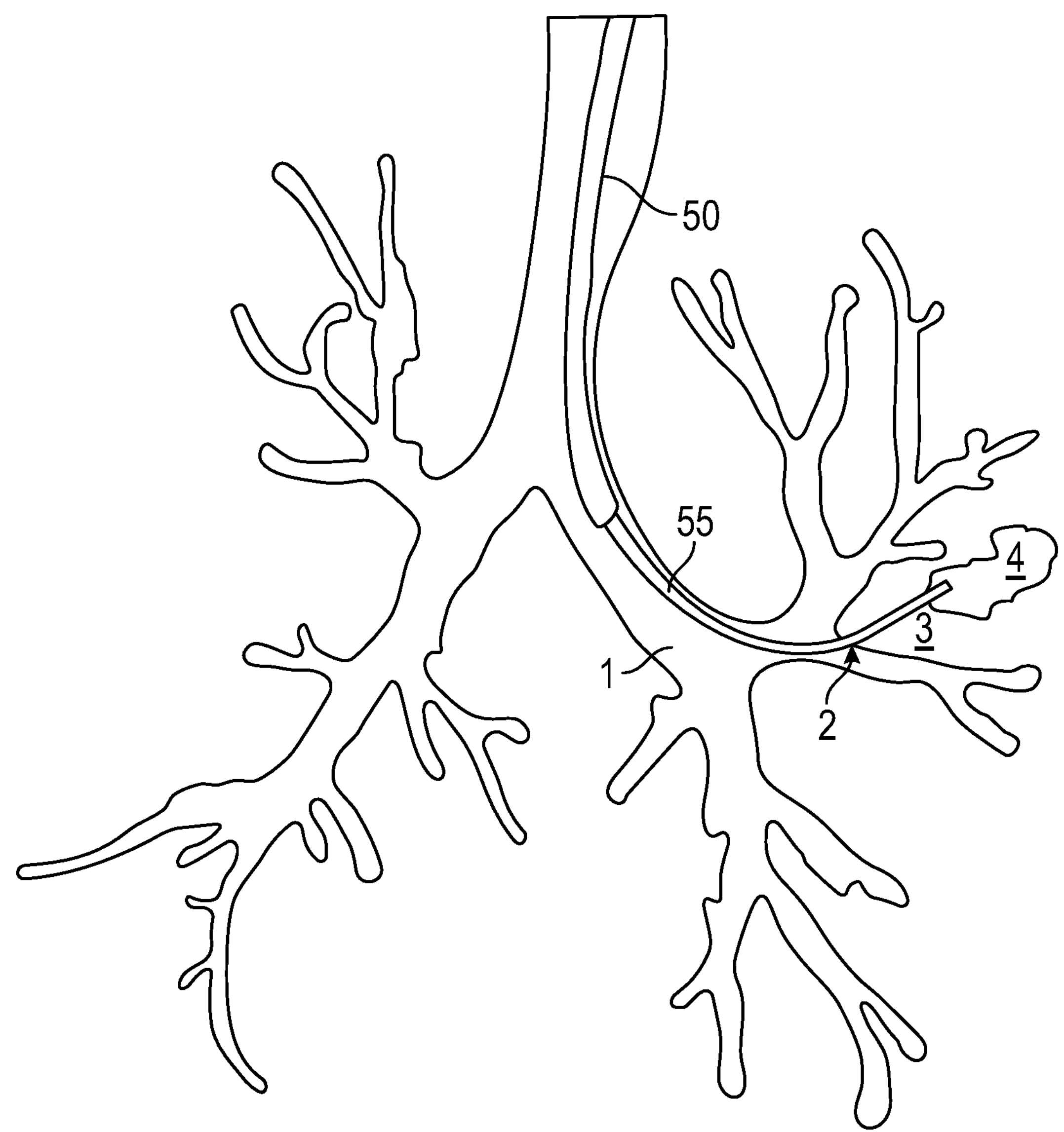
FIG. 1A depicts a schematic view of an endoscope and a catheter (and/or EWC) navigated through a lung of a patient to a target tissue as described in at least one embodiment herein.
Figure 1B:
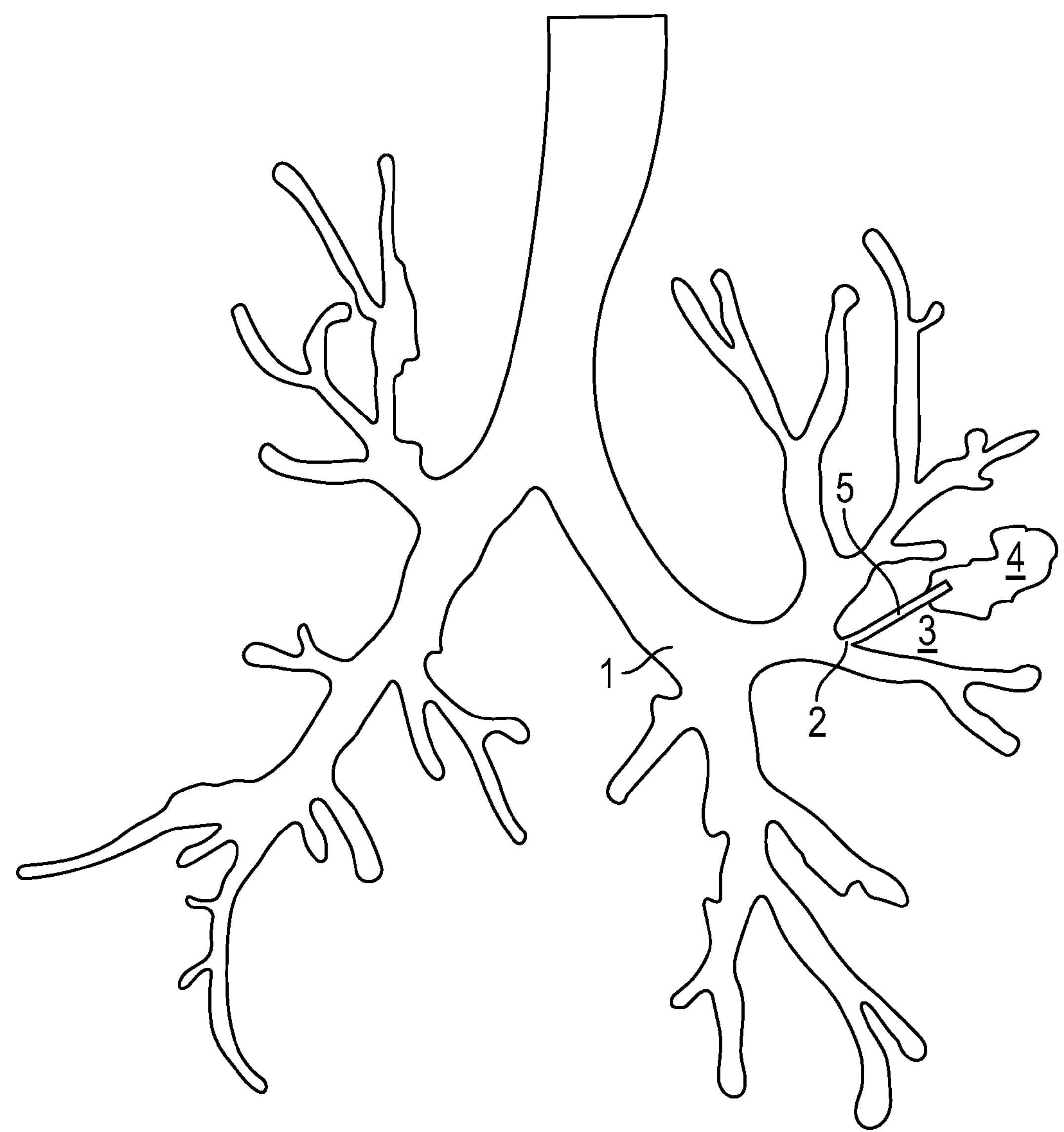
FIG. 1B depicts a schematic view of the lung of FIG. 1A following removal of the navigated an endoscope and a catheter (and/or EWC), as described in at least one embodiment herein.

The present disclosure describes an implantable channel guide configured to be deployed through at least a portion of an airway of a patient to a target tissue. The deployable guide is designed to be implanted in the airway for a temporary period of time (e.g., days, weeks, or months, between multiple surgical procedures) to avoid having to renavigate to the target tissue. The deployable guide maintains a path and/or acts as a trail to the target tissue for the future delivery of endoscopic surgical tools thereto.

As shown in FIGS. 2A-2D, in some embodiments, an implantable channel guide 10 may include a lumen 15 extending longitudinally therethrough. The implantable channel guide 10 may be configured to be deployed within a natural airway 1, an airway wall 2, peripheral tissue 3 exterior the airway wall 2, and/or a target tissue 4. The guide 10 includes an elongate body 12 extending between a proximal end portion 12*a* and a distal end portion 12*b* with the lumen 15 extending therebetween. At least one snare 20 extends from the proximal end portion 12*a*, and at least one anchor member 30 extends from the distal end portion 12*b* of the elongate body 12. The snare 20 is designed to assist with the physical removal of the channel guide 10 from the patient. The snare 20 extends in a proximal direction from the proximal end portion 12*a* of the body 12. The anchor member 30 is configured to secure the distal end portion 12*b* of the guide 10 to the peripheral tissue 3 and/or the target tissue 4. The anchor member 30 extends in a distal direction from the distal end portion 12*a* of the body 12.

As further shown in FIGS. 2A-2D, in some embodiments, the body 12 may be a porous tubular elongate body 12. The porous tubular elongate body 12 may be formed from a plurality of yarns 14 wrapping circumferentially around the lumen 15 in a crisscrossing configuration and circumferentially spaced about the length of the body 12 to define a plurality of surface pores 18 therebetween. The surface pores 18 represent a majority of the outer surface area defined by the tubular body 12 and the yarns represent a minority of the outer surface area defined by the tubular body 20 to maintain gas exchange therethrough while retained within an airway of a patient. In some embodiments, the surface pores 18 represent greater than 75%, and more particularly greater than 85% of the outer surface area defined by the tubular body 12.

The yarns may be monofilament or multifilament yarns of any suitable biocompatible material. The yarns 14 may be braided, woven, knitted, crocheted, and/or embroidered to wrap circumferentially around the lumen 15 to form the porous tubular elongate body 12. Some non-limiting examples of biocompatible materials may include polytetrafluoroethylene (PTFE), nylon (polyamides), block copolymers such as Arnitel® (elastomeric thermoplastic copolyesters) or Pebax® (elastomeric thermoplastic polyether-polyamide block copolymers), polyethylene glycol (PEG), polylactic acid, (PLA), poly-L-lactide (PLLA), poly-D-lactide (PDLA) and poly-DL-lactide (PDLLA), polyglycolic acid (PGA), or polyglycolide (PG), poly(lactic-co-glycolic acid), caprolactone, poly(glycolide-co-caprolactone), poly (trimethylene carbonate), poly(glycolide-co-trimethylene carbonate) and combinations thereof. The yarns may be made of one or more bioresorbable materials, non-bioresorbable materials, or both.

In some embodiments, the guides described herein may be made of a resorbable material configured to resorb over a period of time greater than the anticipated period of time between the initial surgical procedure and any subsequent procedures. In such embodiments, it is envisioned that the resorbable guide may be designed to be left within the body even if a subsequent procedure is later determined not to be necessary, such as might occur after receiving a negative or benign diagnostic result from the first surgical procedure. Such a resorbable guide may be retained within the patient following the ENB with the knowledge the guide can either be physically removed following a subsequent or successive surgical procedure, if necessary, or may simply left to resorb over time, if no additional surgical procedures are required.

Figure 2A:
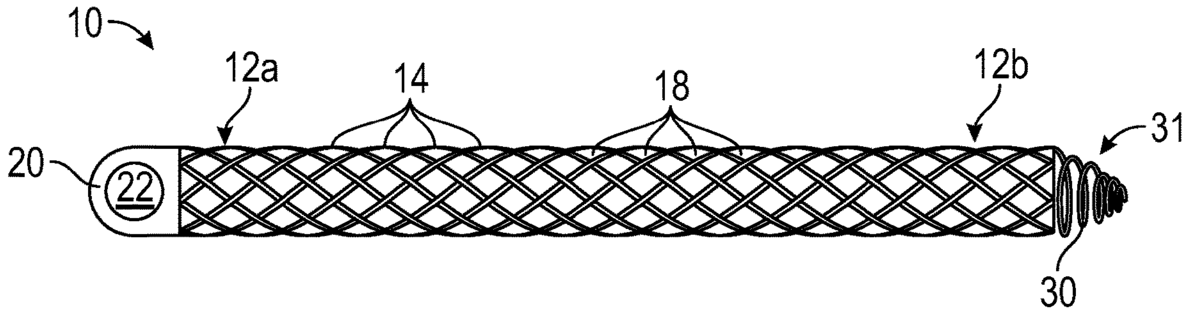
FIG. 2A depicts a top view of a channel guide as described in at least one embodiment herein.
Figure 2B:
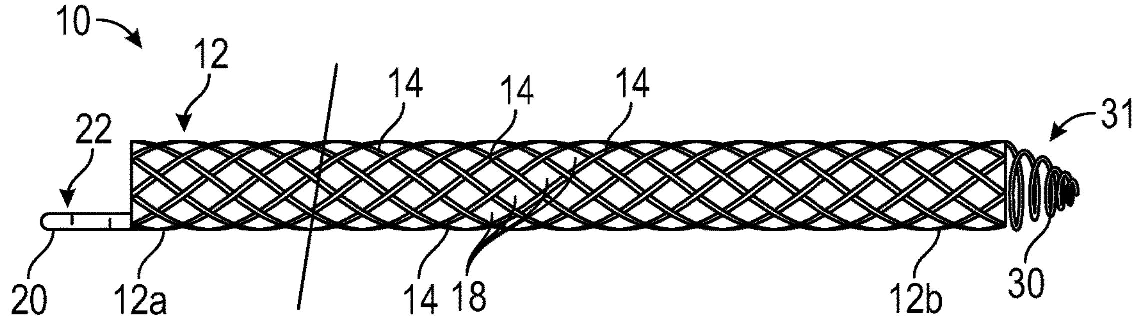
FIG. 2B depicts a side view of the channel guide of FIG. 2A, as described in at least one embodiment herein.
Figure 2C:
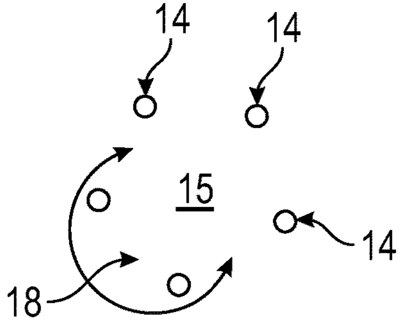
FIG. 2C depicts a cross-section of the channel guide of FIG. 2B along line C-C, as described in at least one embodiment herein.
Figure 2D:
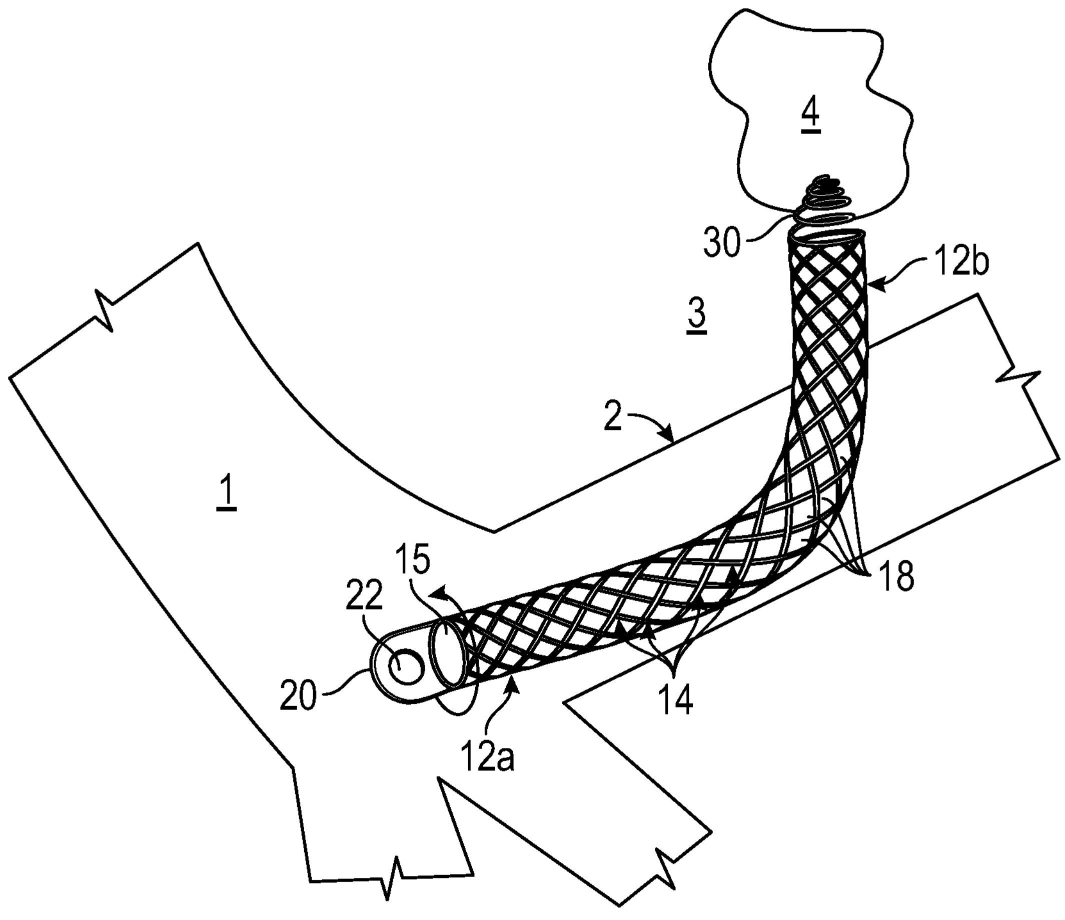
FIG. 2D depicts a schematic view of the channel guide of FIG. 2B retained within at least a portion of an airway of patient's lung, as described in at least one embodiment herein.

As shown particularly in FIGS. 2A and 2D, the proximal end portion 12*a* may include one or more loop snares 20 defining an opening 22 therethrough designed to be grabbed and/or pulled upon to withdraw the guide 10 from the patient. It is envisioned that an endoscopic surgical tool such as a forceps or grasper can be passed through an endoscope to engage the snare for removal of the guide. The snare 20 may also be used to rotate the guide 10 in any direction to introduce the guide 10 into the patient's airway 1, airway wall 2, peripheral tissue 3, and/or target tissue 4, as well as withdraw the guide 10 from the patient's airway 1, airway wall 2, peripheral tissue 3, and/or target tissue 4.

The snare 20 may be made of any biocompatible material. In some embodiments, the snare 20 and the body 12 are formed as a monolithic structure made of the yarns 14 as described herein that form the porous tubular elongate body 12. In such embodiments, the snare 20 may be braided, woven, knitted, crocheted, and/or embroidered to the porous body 12.

In some embodiments, the snare 20 may be formed separate from the porous body 12 and secured the body 12 thereafter. In such embodiments, the snare 20 may be made of a molded, cast, and/or extruded biocompatible material which can be affixed to the body 12 via stitching, adhesives, welding, pressing, and the like.

The loop snare 20 is depicted as generally circular in shape defining a generally circular opening 22. However any shape and/or combinations of shapes may be used. For example, the snare and/or the opening may define a generally elliptical, triangular, rectangular, pentagonal, hexagonal, heptagonal, octagonal shape.

As further shown particularly in FIGS. 2A and 2D, the distal end portion 12*b* may include a corkscrew anchor member 30 defining a spiral configuration that narrows distally to a point 31. The corkscrew anchor member 30 is configured to screw into and/or through an airway wall 2, peripheral tissue 3, and/or target tissue 4 when rotated. The corkscrew anchor member 30 renders the guide 10 self-feeding in that advancement of the guide 10 occurs as the anchor member is rotated and thus no additional longitudinal or radial forces need be applied to the guide 10 to advance the guide 10 into the patient.

In some embodiments, the point 31 may include a cutting edge to further enhance the anchor members 30 ability to penetrate the airway wall 2, peripheral tissue 3, and/or target tissue 4. The cutting edge may be sharp or blunt.

As shown in FIG. 2D, the porous tubular elongate body 12 may be configured to be positioned within and/or extend through a portion of a patient's airway 1 (e.g., bronchi, bronchioles, air sacs, etc.). As further depicted, the porous tubular elongate body 12 may also pass through the airway wall 2 and through the peripheral tissue 3 and/or target tissue 4. Since at least a majority, if not greater than 75%, 85% or 90% of the guide 10 is porous, the guide 10 is designed to define a lumen longitudinally while also allowing air to freely pass therethrough without interfering with a patient's ability to inhale and/or exhale air while the guide 10 is temporarily implanted in a patient's airway 1.

By extending a length in the patient's airway (as opposed to a plug device designed to sit generally only in the opening of an airway so as not to block any portion of the airway), the porous guide 10 is easily located upon reentry of the airway 1 at a later date. In addition, by extending through the airway wall 2 to the target tissue 4, the guide 10 provides a trail for the surgical tools to follow to arrive back at the target tissue 4 during any subsequent procedures.

In some embodiments, the body 12 may be rotated (as indicated by the arrow in FIG. 1D) around a longitudinal axis of the body 12 to position and/or screw the guide 10 into a patient's airway 2 and/or tissue 3, 4. The one or more snares 20 may be further designed to assist with the rotating of the body 12 during insertion and/or removal of the guide 10.

In some embodiments, the guide 10 may be self-feeding into the tissue 3, 4 where upon rotation of the guide 10 in a first direction (e.g., clockwise or counter clockwise) will cause the corkscrew anchor member 30 to advance the guide 10 forward into the airway 2 and/or tissue 3, 4. In some embodiments, the guide 10 may be withdrawn from the airway 2 and/or tissue 3, 4 by rotating the guide 10 in a second direction opposite the first direction (e.g., counter clockwise or clockwise, respectively).

Figure 3:
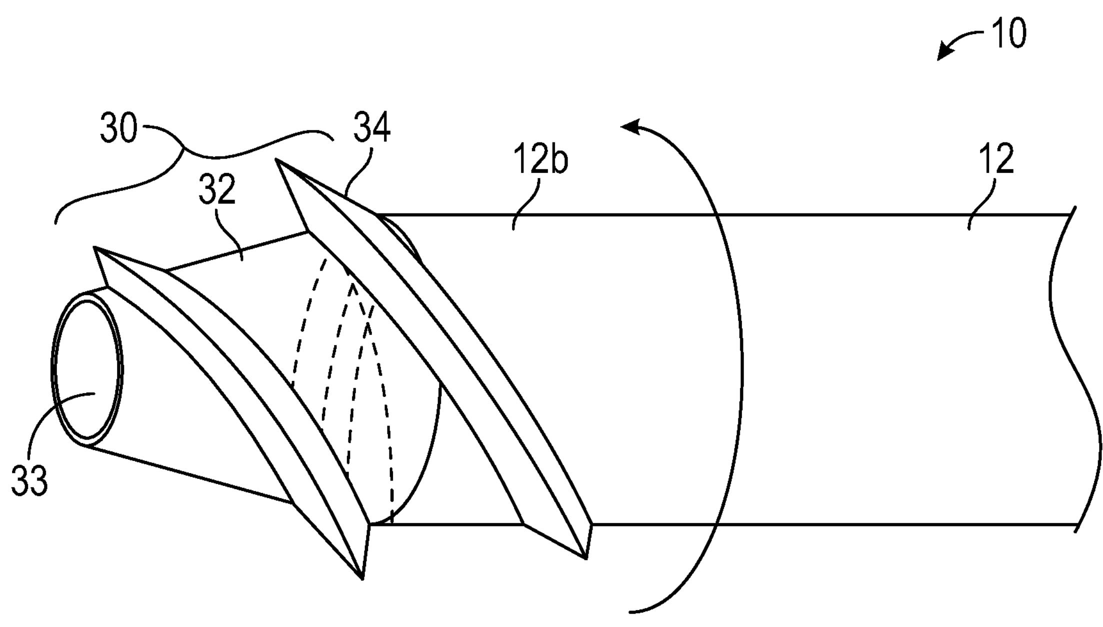
FIG. 3 depicts a schematic side view of a distal end portion of a channel guide as described in at least one embodiment herein.

As depicted in FIG. 3, in some embodiments, the distal end portion 12*b* of the body 12 may include a threaded anchor member 30 defining an anchor body 32 including one or more threads 34 wrapped circumferentially around the anchor body 32. The anchor body 32 may narrow distally and may define an anchor lumen 33 therethrough. The anchor lumen 33 is configured to receive, maintain, and/or pass endoscopic surgical tools therethrough. The threaded anchor member 30 is configured to screw into and/or through an airway wall 2, peripheral tissue 3, and/or target tissue 4 when rotated (as indicated by the arrow). The threaded anchor member 30 renders the guide 10 self-feeding in that advancement of the guide 10 occurs as the anchor member is rotated and thus no additional longitudinal or radial forces need be applied to the guide 10 to advance the guide 10 into the patient.

In some embodiments, the thread 34 may be one continuous thread. In some embodiments, the thread 34 may be a plurality of intermittent threads spaced circumferentially around the anchor body 32.

Figure 4:
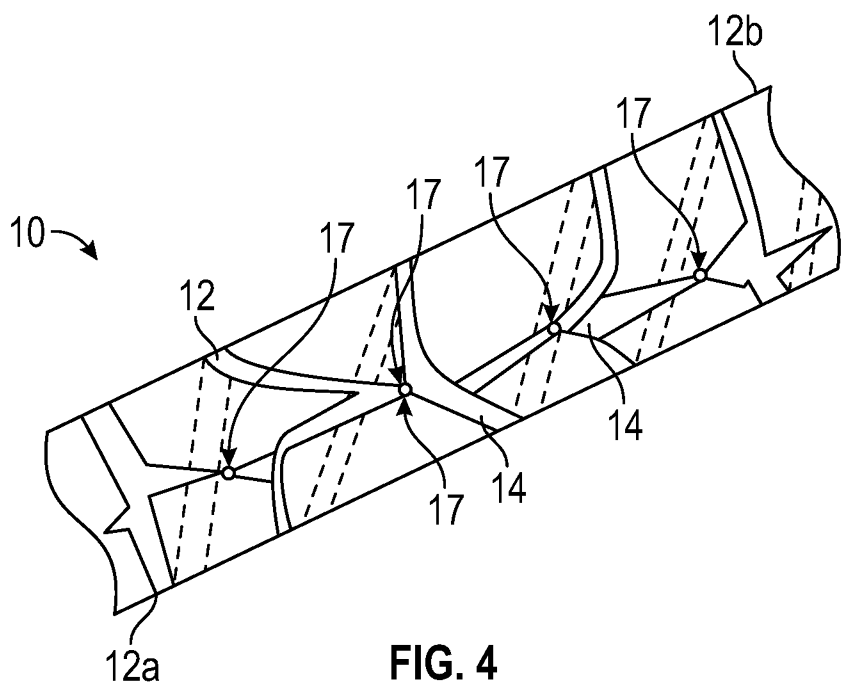
FIG. 4 depicts a schematic side view of a portion of a channel guide as described in at least one embodiment herein.

As depicted in FIG. 4, in some embodiments, the porous tubular elongate body 12 may further include one or more necked portions 17 positioned intermittently along a length of the body 12 (and/or yarns 14). In some embodiments, the necked portions 17 may be lengthening neck portions configured to lengthen when pulled upon, causing the body 12 (and/or yarn 14) to lengthen and narrow for easier removal from the patient's airway.

In some embodiments, the necked portions 17 may be tearable necked portions 17 configured to include a weakened link, such as a molded, etched, or laser-weakened link, between neighboring surface pores 18 such that when pulled upon, a first portion of the body 12 (and/or yarns 14) will separate from a second portion of the body 12 (and/or yarn 14) for easier removal from the patient's airway. In some embodiments, the tearable neck portions 17 may be placed on the portion of the body 12 (and/or yarn 14) that passes through the airway wall 2. In such embodiments, pulling on the body 12 may cause the proximal end portion 12*a* of the body 12 to separate from the distal end portion 12*b* withdrawing the proximal end portion 12*b* from the airway of the patient while leaving the distal end portion 12*b* positioned in at least one of the airway wall 2, peripheral tissue 3, or target tissue 4 while leaving only a portion of the elongate body within the airway 1.

In some embodiments, the guide 10 includes both a corkscrew anchor member 30 and necked portions 17 intermittently spaced along the guide 10. In such embodiments, the body 12 of the guide 10 may be configured to compress when rotated in a first direction to introduce the guide 10. Compression of the guide 10 reduces the diameter of the lumen 15 of the body 12 and/or prevents the necked portions 17 from being tensioned to lengthen or tear away from each other during insertion. The body 12 of the guide 10 may be further configured to expand or unfurl when rotated in a second opposite direction to withdraw the guide 10 from the patient and/or create tension on the necked portion 17 causing the necked portions to lengthen and/or tear away from each other during removal.

Turning to FIGS. 5A-6D, additional embodiments of an implantable channel guide are shown. In FIGS. 5A-5E, in some embodiments, the guide 110 includes a porous tubular elongate body 112 formed from a plurality of rods 114 circumferentially spaced about the body 112 and connected to each other by a plurality of transverse ribs 116 longitudinally spaced along the body 112 and/or the rods 114. The rods 114 and ribs 116 define a lumen 115 that extends along a longitudinal axis $A_1$ from a proximal end portion 112*a* to a distal end portion 112*b* of the body 112. The lumen 115 is configured to receive, maintain, and/or pass endoscopic surgical tools therethrough.

As further depicted in FIGS. 5A-5E, in some embodiments, the plurality of rods 114 may be generally parallel to each other and/or the plurality of the transverse ribs 116 may be generally parallel to each other. However, in some embodiments, at least one of the rods 114 and/or at least one of the ribs 116 may not be parallel to the other rods 114 or ribs 166, respectively. Various different configurations of ribs and rods are envisioned.

At least one snare 120, defining an opening 122, extends in a proximal direction from the proximal end portion 112*a* of the body 112. The opening 122 of the snare 120 defines a transverse axis $A_2$ being generally perpendicular to the longitudinal axis $A_1$ of the lumen 115 of the body 112.

Figures 5A, 5B, 5C, 5D:
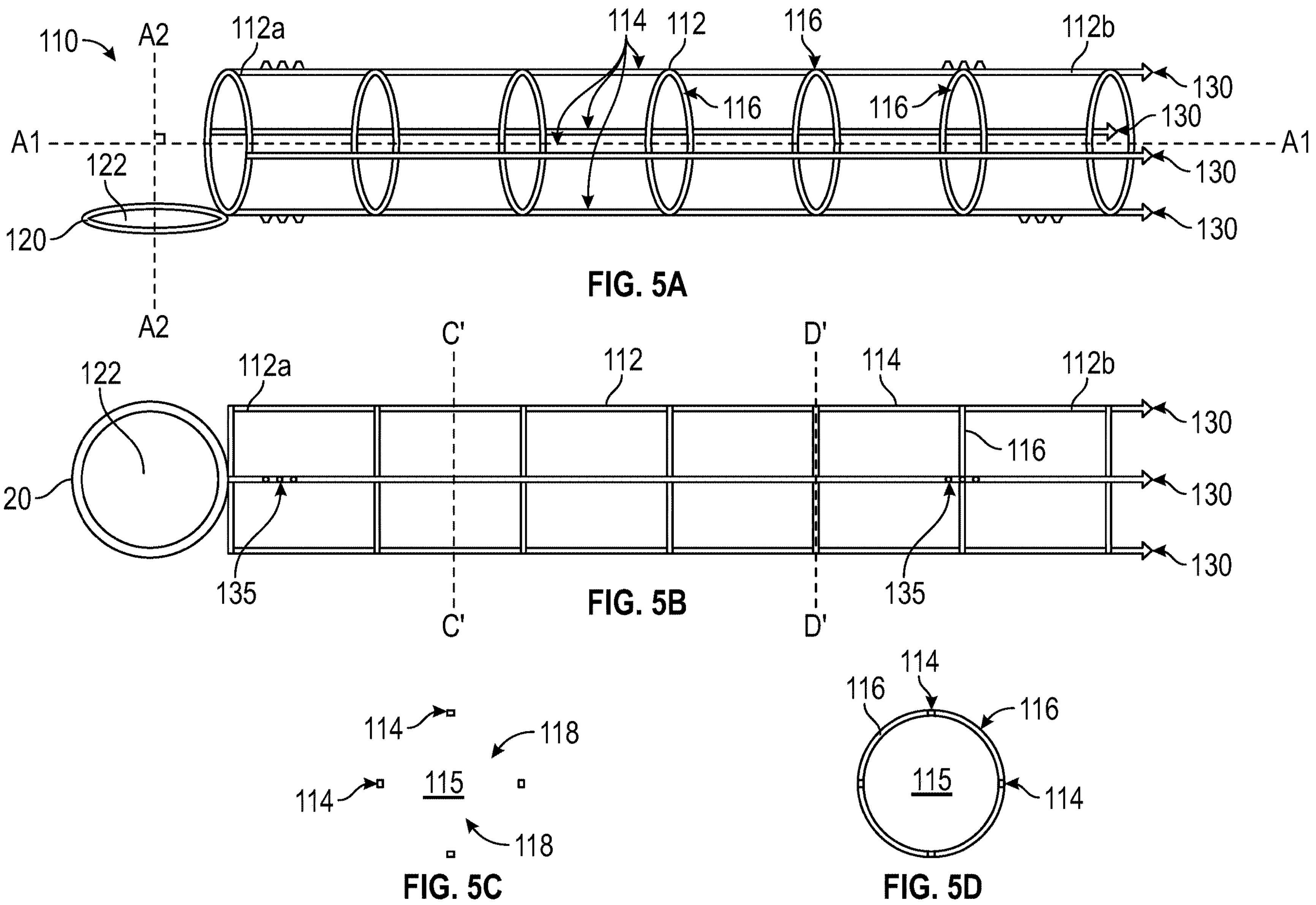
FIG. 5A depicts a perspective view of a channel guide as described in at least one embodiment herein.
FIG. 5B depicts a top view of the channel guide of FIG. 5A, as described in at least one embodiment herein.
FIGS. 5C and 5D depict a cross-section of the channel guide of FIG. 5B along lines C'-C' and D'-D', respectively, as described in at least one embodiment herein.
Figure 5E:
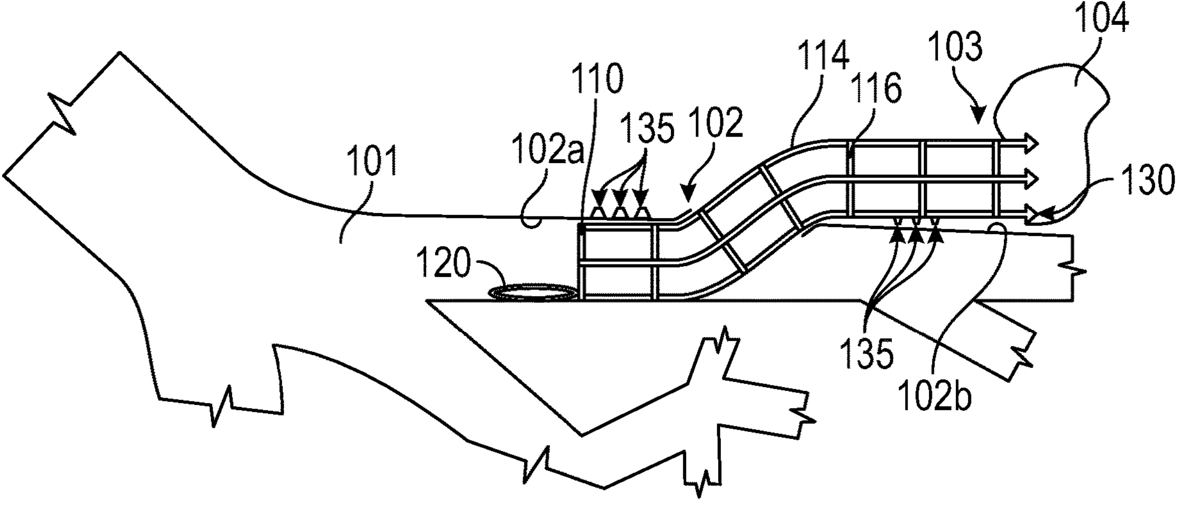
FIG. 5E depicts a schematic view of the channel guide of FIG. 5B retained within at least a portion of an airway of patient's lung, as described in at least one embodiment herein.

At least one anchor member 130 extends in a distal direction from the distal end portion 112*b* of the body 112. In some embodiments, the anchor member 130 includes a plurality of barbs or tines extending generally longitudinally (FIGS. 5A and 5B). In such embodiments, the guide 110 may be designed to be simply advanced or pushed into the tissue, i.e., without rotation, to allow the anchor member 130 to engage a patient's tissue 103 and/or 104.

As further shown in FIGS. 5A and 5B, in some embodiments, the porous tubular elongate body 112 as described herein may further include one or more crenulations 135 positioned thereon and extending away from the lumen 115 and/or generally perpendicular to the anchor member 130. The crenulations 135 configured to engage the wall of an airway 102, a peripheral tissue 103, and/or a target tissue 104 positioned along a side of the body 112.

The body 120 also defines a plurality of surface pores 118 on an outer circumference or perimeter of the body 112. The pores 118 defined between neighboring rods 114 and neighboring ribs 116. The pores 118 and/or the lumen 115 are configured to render a majority of the body 112 open to maintain the exchange of gas in and out of the airway while the guide 110 is temporarily implanted at least partially in the airway.

In some embodiments, at least 80% of the surface area defined by the body 112 is open via the surface pores and/or less than 20% of the surface area defined by the body 112 constitute structural elements, i.e., rods, ribs, etc. In some embodiments, at least 85% of the surface area of the body 112 is open via the surface pores and/or less than 15% of the surface area of the body 112 represents any structural elements, i.e., rods, ribs, etc. In some embodiments, at least 90% of the surface area of the body 112 is open via the pores and/or less than 10% of the surface area of the body 112 represents any structural elements, i.e., rods, ribs, etc.

As shown in FIG. 5D, the channel guide 110 is designed to be positioned within a patient's airway 101 through an airway wall 102 into a peripheral tissue 103 near the airway

101 and/or a target tissue 104. In some embodiments, the diameter of the lumen 115 may be generally equal to the diameter of the airway 101 thereby engaging an inner surface 102*a* of the airway wall 102. In such embodiments, the crenulations 135 on the proximal end portion 112*a* of the body may engage the inner surface 102*a* of the airway wall 102 to aide in securing the guide 110 to a fixed position within the airway 101. In some embodiments, the crenulations 135 on the distal end portion 112*b* of the body may engage the outer surface 102*b* of the airway wall 102 and/or the peripheral tissue 103 to aide in securing the guide 110 to a fixed position between the airway 101 and the target tissue 104.

Turning to FIGS. 6A-6D, in some embodiments, a proximal end portion 212*a* of a body 212 of a channel guide 210 is a porous tubular elongate body and a distal end portion 212*b* of the body 212 is less porous than the proximal end portion 212*a* and/or a non-porous distal end portion 212*b*. Such a configuration allows the proximal end portion 212*a* to remain in the airway of a patient without interfering with a patient's ability to breathe while the distal end portion 212*b* is configured to prevent encroachment of the peripheral tissue 203 and/or target tissue 204 into the lumen 215 while retained outside the airway. As the time increases in which the guide 210 is implanted in the airway wall 202, peripheral tissue 203, and/or target tissue 204, the more likely at least one of the airway wall 202, the peripheral tissue 203, or the target tissue 204 will encroach upon or block the lumen 215. However, since the distal end portion 212*b* of the tubular body 12 is positioned exterior to the airway 201, the distal end portion 212*b* may not need to be predominantly open and/or porous because no air needs to pass therethrough. In such embodiments, it may be more beneficial to maintain the lumen 215 in the distal end portion 212*b* rather than allow air to pass therethrough. Thus, in some embodiments, the distal end portion 212*b* of the tubular body 12 may be non-porous or less porous than the proximal end portion 212*a* of the body 212.

Figures 6A, 6B, 6C:
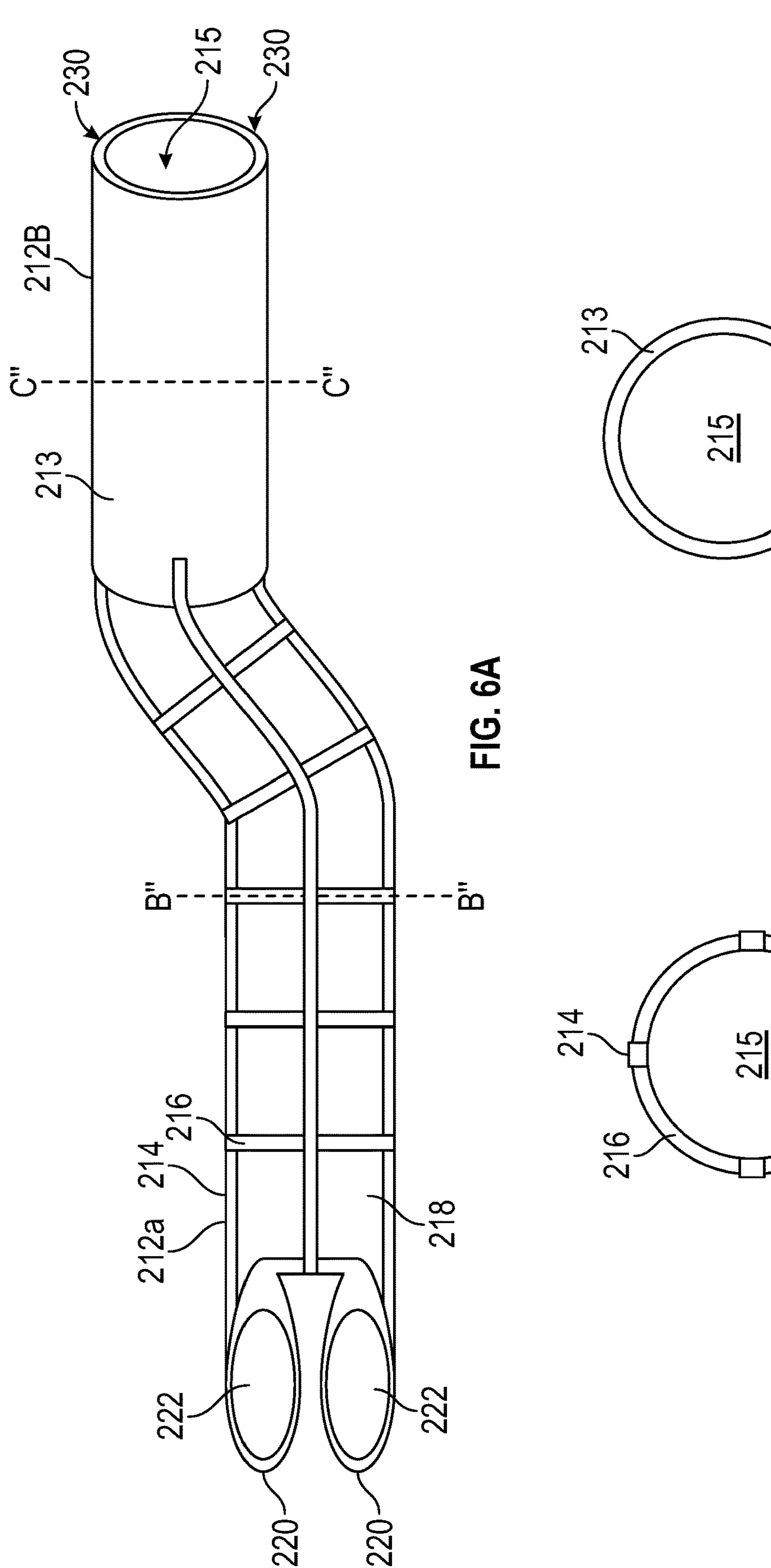
FIG. 6A depicts a perspective view of a channel guide as described in at least one embodiment herein.
FIGS. 6B and 6C depict a cross-section of the channel guide of FIG. 6A along lines B"-B" and C"-C", respectively, as described in at least one embodiment herein.
Figure 6D:
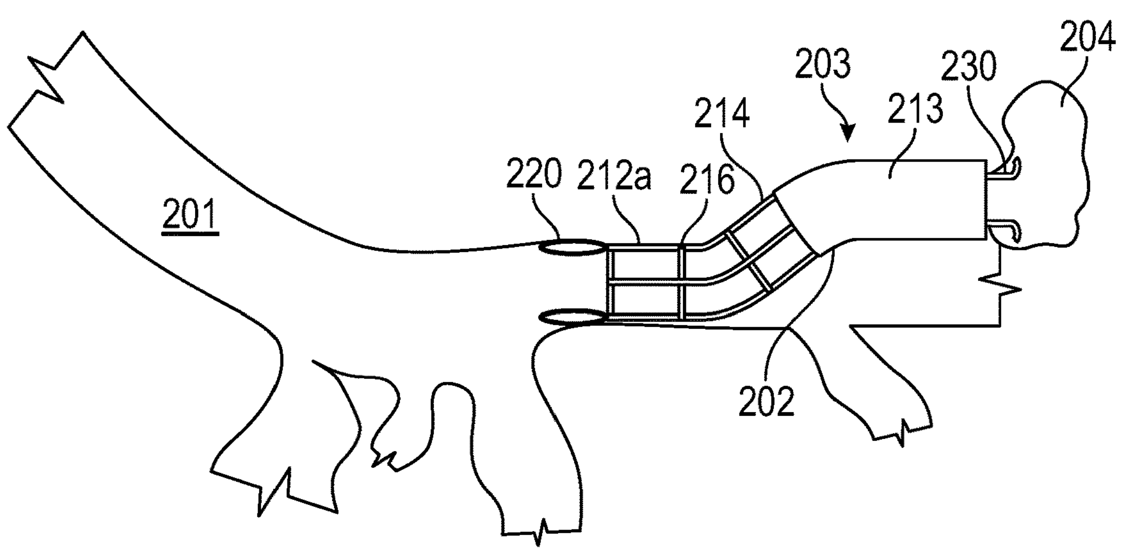
FIG. 6D depicts a schematic view of the channel guide of FIG. 6A retained within at least a portion of an airway of patient's lung, as described in at least one embodiment herein.

As further shown in FIGS. 6A and 6D, in some embodiments, the porous proximal end portion 212*a* may be formed from a plurality of rods 214 circumferentially spaced about the proximal end portion 212*a* and connected to each other by a plurality of transverse ribs 216 longitudinally spaced along the proximal end portion 212*a* and/or the rods 214. The rods 214 and ribs 216 define lumen 215 on the proximal end portion 212*a* of the body 212.

The non-porous distal end portion 212*b* may be formed from a non-porous tubular sidewall 213. The sidewall 213 defines the lumen 215 on the distal end portion 212*b* of the body 212.

In some embodiments, the porous proximal end portion 212*a* may be formed from a flexible material and the non-porous distal end portion 212*b* may be made from a stiff and/or less flexible material than the proximal end portion 212*a*.

As further shown in FIGS. 6A and 6D, in some embodiments, the guide 210 may further include two or more snares 220 extending proximally from the proximal end portion 212*a* of the body 212. Each snare 220 defining an opening 222. The guide 210 may also further include two or more anchor members 230 extending distally from the distal end portion 212*b* of the body 212. The anchor members 230 may be hooks.

Figure 7:
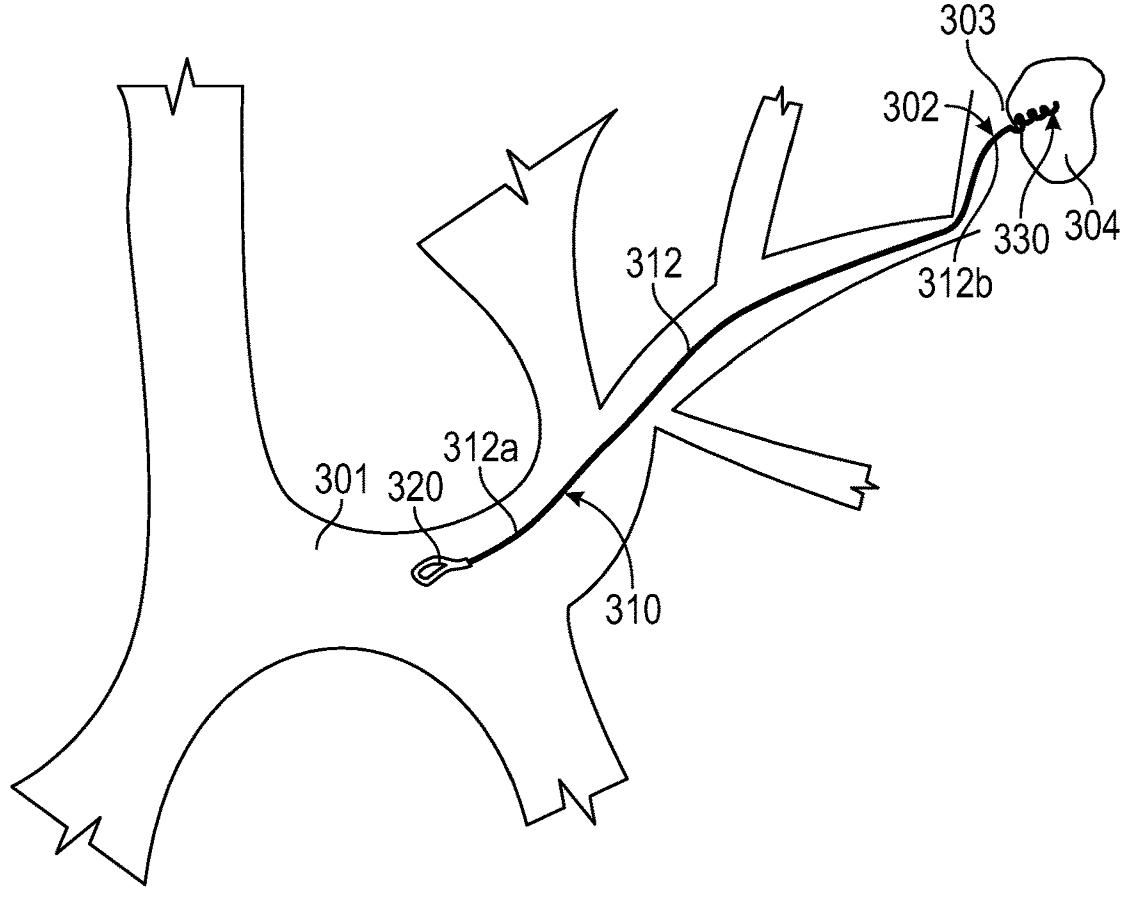
FIG. 7 depicts a schematic view of a channel guide retained within at least a portion of an airway of patient's lung, as described in at least one embodiment herein.

Turning to FIG. 7, in some embodiments the guide 310 may be an implantable channel guide 310 configured to pass endoscopic surgical tools over the channel guide 310 (as opposed to through a lumen of the channel guide). In such embodiments, the channel guide 310 may be free of a lumen extending therethrough.

In some embodiments, the implantable guide 310 may include an elongate body 312 free of a lumen including one or more snares 320 (e.g., loops, eyelets, barbed loops, etc.) on a proximal end portion 312*a* thereof and one or more anchor members 330 (e.g., barbs, tines, hooks, corkscrews, etc.) on a distal end portion 312*b* of the elongate body 312. In some embodiments, the lumen-free elongate body 312 may be formed from one or more yarns braided, woven, knitted, crocheted, and/or embroidered together. In some embodiments, the lumen-free elongate body 312 may be formed from one or more of casting, pressing, and/or extruding.

In some embodiments, the lumen-free channel guide 310 may be a V-loc suture. In some embodiments the lumen-free channel guide 310 may include a proximal loop snare 320 and elongate body 312 similar to a V-loc suture, with a corkscrew anchor member 330 positioned on a distal end portion 312*b* thereof. The elongate body 312 of the lumen-free channel guide 310 may or may not be porous because the diameter may be significantly smaller than the diameter of the airway and as such the guide 310 may not be of sufficient size to extend across and/or block the airway 301.

The lumen-free channel guides 310 described herein may provide a trail from a patient's airway 301 through an airway wall 302 and a peripheral tissue 303 to a target tissue 304. The endoscopic surgical tools may be configured to follow the guide 310 by passing over the lumen-free channel guide 310. In some embodiments, the surgical tool may include a lumen configured to receive and pass the channel guide therethrough as the instrument is led to the target tissue by sliding over the guide.

In some embodiments, different portions of the guides described herein may be formed of different materials, stiffness, opacity, strength, and/or color. For example, in some embodiments, the snare and/or anchor member of the guide may display a different color and/or radiopacity than the body of the guide in order to render the snare and/or anchor member more visible to the naked eye and/or a scanning device than the body for proper placement, easier removal, and/or easier manipulation/rotation of the guide. In other examples, in some embodiments, the snare and/or anchor member of the guide may display a higher degree of stiffness and/or strength than the body of the guide in order to allow the body to be more easily contorted to extend through a non-linear passageway inside the patient and/or decrease the likelihood of damaging the snare and/or anchors when manipulated and/or penetrating directly into tissues.

The channel guides as described herein may further include one or more bioactive agents. The bioactive agents may be applied to as a coating and/or incorporated into any portion of the channel guides described herein. The bioactive agent may represent less than 10% by weight and particularly less 5% by weight of the channel guide.

Suitable examples of bioactive agents include, for example, antimicrobial agents, antibiotics, antiviral agents, anti-proliferatives, chemotherapeutics, steroids, anti-clotting agents, clotting agents, analgesics, anesthetics, anti-inflammatory agents, antiasthmatics agents, mucolytics, antihistamines, decongestants, wound repair agents, biologics, protein therapeutics, monoclonal or polyclonal antibodies, DNA, RNA, peptides, polysaccharides, lectins, lipids, probiotics, vitamins, herbs, diagnostic agents, dyes, and combinations thereof. In some embodiments, the bioactive agent may be selected from the group consisting of doxorubicin, irinotecan, sorafenib, adriamycin, daunomycin, mitomycin, cisplatin, epirubicin, methotrexate, 5-fluorouracil, aclacinomycin, nitrogen mustard, cyclophosphamide, bleomycin, daunorubicin, vincristine, vinblastine, vindesine, tamoxifen, valrubisin, pirarubicin, mitoxantrone, gemcitabine, idarubicin, temozolomide, paclitaxel, dexamethasone, aldesleukin, avelumab, bevacizumab, carboplatin, regorafenib, docetaxel, doxil, gefitinib, imatinib mesylate, herceptin, imatinib, aldesleukin, pembrolizumab, nivolumab, mitomycin C, olaparib, pembrolizumab, rituximab, sunitinib, atezolizumab, lapatinib and ipilimumab. In some embodiments, the bioactive agent is selected from paclitaxel, nivolumab, and/or ipilimumab. In some embodiments, the bioactive agent is paclitaxel.

In some embodiments, one or more bioactive agents may be concentrated on the one or more anchor members of the channel guide. In such embodiments, the bioactive agent is likely to directly interact with the target tissue via the anchor member attaching thereto. For example, the one or more anchor members may include one or more chemotherapeutic and/or anti-proliferative agents, including but not limited to, paclitaxel, nivolumab, and/or ipilimumab.

In some embodiments, one or more of the bioactive agents may be located on the elongate body and/or snare(s). In such embodiments, the bioactive agent is likely to interact with the patient's airway and/or inner airway wall while retained therein. For example, the elongate body and/or snare(s) may include but not limited to antiasthmatic agents, steroids, mucolytics, antihistamines, decongestants, clotting agents, and the like.

Methods of using the channel guides described herein are also provided. In some embodiments, a surgical method is provided including a least the following: navigating at least one of an endoscope, catheter, or EWC through an airway of a patient to a target tissue beyond the airway; deploying an implantable channel guide via the at least one endoscope, catheter or EWC through a length of the airway to the target tissue; and removing the at least one endoscope, catheter or EWC from the airway.

In some embodiments, the step of navigating may be performed using an electromagnetic navigation system. In some embodiments, the step of navigating may be performed via EBN. In some embodiments, the step of navigating may further include tunneling of at least one of the endoscope, catheter, or EWC, through an airway wall and peripheral tissue of the airway wall to the target tissue creating a channel from the airway through the peripheral tissue to the target tissue.

In some embodiments, the methods described herein may further include examining of the target tissue after the step of navigating and before the step of deploying the guide. Examination of the target tissue may include biopsying the target tissue.

In some embodiments, the step of deploying the channel guide includes deploying the guide within the airway, through the airway wall, through the channel created, and anchored to at least one of the target tissue, an exterior of the airway wall, or the peripheral tissue of the airway. In some embodiments, the channel guide can be rotated via a proximal snare positioned thereon to self-feed into the airway wall and/or tissues exterior thereto.

In some embodiments, the method may further include pushing the channel guide longitudinally out of the distal end of the endoscope, catheter, or EWC as the endoscope, catheter, or EWC is withdrawn from the airway. In such embodiments, the method may further comprise radially compressing the channel guide, to reduce the thickness of the elongate body, prior to inserting the guide through at least one of the endoscope, catheter, or EWC. In such embodiments, the method may further include radially expanding the channel guide upon exiting at least one of the endoscope, catheter, or EWC. For example, in some embodiments, the guide may be formed of a material and/or designed structurally to be reduced radially in size to be inserted through at least one of the endoscope, catheter, or EWC (under compression) and further configured and/or designed structurally to expand upon removal thereof.

In some embodiments, the surgical method may further include: performing one or more subsequent surgical procedures wherein one or more endoscopic surgical tools are passed either through or over the channel guide to the target tissue; and/or, removing the channel guide from the patient after a final subsequent surgical procedure is performed. In some embodiments, at least one of the subsequent surgical procedures may include treating the target tissue via resection surgery, tissue ablation, supplemental biopsy, applying dyes or bioactive agents directly to target tissue, and/or radioactive treatment. In some embodiments, removal of the channel guide may be performed using surgical forceps or a grasper to grab the snare and withdrawing the snare via the forceps or grasper. In some embodiments; the guide may be rotated in a second direction opposite the first direction to withdraw and/or unscrew the guide from the airway.

In some embodiments, the channel guides described herein may further include one or more identifying items, such as a serial number, bar code, and/or QR code applied thereto it is envisioned that the identifying item may be registered with a surgical navigation system so that the planned pathway can be easily recalled based on the identifying item saving time by providing a starting point for renavigation in the vicinity of the original navigation process wherein the proximal end portion of the channel guide should be readily visible by extending a length inside the airway near the point of previously exiting the airway.

The channel guides described herein are configured to help locate and renavigate endoscopes, catheters, EWCs and/or surgical tools to a repeatable proper alignment to a target tissue. The surgical tools may be selected from the group consisting of a locating guide, an imaging device, a guidewire, a surgical balloon, a biopsy forceps, surgical grasper, a cytology brush, an aspirating needle, an applicator, a sprayer, an ablation device, resection tools, radiation devices and/or sensors, and combinations thereof.

The channel guides described herein may also be included in a kit. In some embodiments, a kit may include at least one channel guide as described herein and optionally at least one of an endoscope, such as a bronchoscope, a catheter, a EWC, a surgical navigation system, and/or an endoscopic surgical tool. The channel guide alone and/or in a surgical kit is configured to be sterilized using any suitable known method and may be stored in any suitable sterilizable packaging.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting but merely as exemplifications of particular embodiments. Those skilled in the art will envision other modifications within the scope and spirit of the claims appended hereto.

What is claimed is:

1. An implantable channel guide configured for deployment at least partially in an airway of a patient comprising:

an elongate body including a lumen extending between a proximal end portion and distal end portion of the elongate body, the proximal end portion of the elongate body configured to be deployed within the airway, the distal end portion of the elongate body configured to be deployed in a peripheral tissue exterior the airway wall, and the lumen configured to pass endoscopic surgical tools therethrough to a target tissue, at least one loop snare extending from the proximal end portion of the elongate body and defining an opening therethrough, the at least one loop snare configured to rotate the elongate body around a longitudinal axis of the elongate body, wherein the at least one loop snare is formed separate from the elongate body;

and at least one corkscrew anchor member extending along a longitudinal axis from the distal end portion of the elongate body, the at least one corkscrew anchor member configured to rotate about the longitudinal axis to advance the distal end portion of the elongate body through the peripheral tissue exterior the airway wall and secure the distal end portion of the elongate body to the target tissue.

2. The implantable channel guide of claim 1, wherein the elongate body comprises a porous tubular elongate body.

3. The implantable channel guide of claim 2, wherein the porous tubular elongate body comprises a plurality of yarns wrapping circumferentially around the lumen in a crisscrossing configuration and spaced about a length of the porous tubular elongate body to define a plurality of surface pores therebetween.

4. The implantable channel guide of claim 3, wherein the plurality of surface pores represent a majority of an outer surface area defined by the porous tubular elongate body and the plurality of yarns represent a minority of the outer surface area defined by the porous tubular elongate body.

5. The implantable channel guide of claim 3, wherein the plurality of surface pores represent at least 85% of an outer surface area defined by the porous tubular elongate body and the plurality of yarns represent at most 15% of the outer surface area defined by the porous tubular elongate body.

6. The implantable channel guide of claim 2, wherein the porous tubular elongate body comprises a plurality of rods connected to a plurality of transverse ribs, the rods extending longitudinally and spaced circumferentially, the ribs extending circumferentially and spaced longitudinally.

7. The implantable channel guide of claim 2, wherein the proximal end portion of the body comprises the porous tubular elongate body and the distal end portion of the body comprises a non-porous tubular elongate body.

8. The implantable channel guide of claim 1, wherein the at least one loop snare comprises two loop snares positioned on opposite sides of the proximal end portion of the body.

9. The implantable channel guide of claim 1, wherein the at least one corkscrew anchor member defines a spiral configuration that narrows distally to a point defining a cutting edge rendering the channel guide self-feeding.

10. The implantable channel guide of claim 1, further comprising one or more necked portions including at least one of an extendable necked portion configured to lengthen when a longitudinal stress is applied thereto or a tearable necked portion configured to fracture when a longitudinal stress is applied thereto.

11. The implantable channel guide of claim 1, further comprising one or more identifying items selected from a serial number, bar code, or QR code applied thereto, the one or more identifying items designed to be registered with a surgical navigation system so that a planned pathway can be easily recalled based on the one or more identifying items.

12. The implantable channel guide of claim 1, further comprising one or more bioactive agents.

13. The implantable channel guide of claim 1, wherein the implantable channel guide is resorbable.

14. A kit comprising:

an implantable channel guide configured to be deployed through at least a portion of a patient's airway to maintain a path through the airway to a target tissue for future delivery of endoscopic surgical tools thereto, the implantable channel guide including:

an elongate body including a lumen extending between a proximal end portion and distal end portion of the elongate body, the proximal end portion of the elongate body configured to be deployed within the airway, the distal end portion of the elongate body configured to be deployed in a peripheral tissue exterior the airway wall, and the lumen configured to pass endoscopic surgical tools therethrough to a target tissue;

at least one loop snare extending from the proximal end portion of the elongate body and defining an opening therethrough, the at least one loop snare configured to rotate the elongate body around a longitudinal axis of the elongate body, wherein the at least one loop snare is formed separate from the elongate body; and at least one corkscrew anchor member extending along a longitudinal axis from the distal end portion of the elongate body, the at least one corkscrew anchor member configured to rotate about the longitudinal axis to advance the distal end portion of the elongate body through the peripheral tissue exterior the airway wall and secure the distal end portion of the elongate body to the target tissue; and at least one of an endoscope, a catheter, an extended working channel (EWC), a surgical navigation system, or an endoscopic surgical tool.

15. A surgical method, wherein an implantable channel guide includes:

an elongate body including a lumen extending between a proximal end portion and distal end portion of the elongate body, the proximal end portion of the elongate body configured to be deployed within an airway of a patient, the distal end portion of the elongate body configured to be deployed in a peripheral tissue exterior the airway wall, and the lumen configured to pass endoscopic surgical tools therethrough to a target tissue;

at least one loop snare extending from the proximal end portion of the elongate body and defining an opening therethrough, the at least one loop snare configured to rotate the elongate body around a longitudinal axis of the elongate body, wherein the at least one loop snare is formed separate from the elongate body; and at least one corkscrew anchor member extending along a longitudinal axis from the distal end portion of the elongate body, the at least one corkscrew anchor member configured to rotate about the longitudinal axis to advance the distal end portion of the elongate body through the peripheral tissue exterior the airway wall and secure the distal end portion of the elongate body to the target tissue; and the surgical method comprising:

navigating at least one of an endoscope, catheter, or extended working channel (EWC) through the airway of the patient to the target tissue beyond the airway;

deploying the implantable channel guide via the at least one endoscope, catheter or EWC through a length of the airway to the target tissue so that the proximal end portion of the elongate body is deployed within the airway and the distal end portion of the elongate body is deployed in the peripheral tissue exterior the airway wall; and removing the at least one endoscope, catheter or EWC from the airway.

16. The method of claim 15, wherein the step of deploying further comprises tunneling through the airway wall and peripheral tissue of the airway wall to the target tissue creating a channel from the airway to the target tissue.

17. The method of claim 16, wherein the implantable channel guide is deployed within the airway, through the airway wall, and through the channel, and anchored to at least one of the target tissue, an exterior of the airway wall, or the peripheral tissue of the airway.

18. The method of claim 15, wherein navigating the at least one of an endoscope, catheter or EWC comprises using an electromagnetic navigation system.

19. The method of claim 15, further comprising performing a subsequent surgical procedure wherein one or more endoscopic surgical tools are passed through the implantable channel guide to the target tissue.

* * * * *